United States Patent [19]

Richman

[11] 4,269,058
[45] May 26, 1981

[54] METHOD AND APPARATUS FOR DETERMINING THE ACCURACY OF A SPHYGMOMANOMETER

[75] Inventor: Stephan S. Richman, Winnetka, Ill.

[73] Assignee: Marshall Electronics, Inc., Skokie, Ill.

[21] Appl. No.: 86,823

[22] Filed: Oct. 22, 1979

[51] Int. Cl.³ .............................................. G01L 27/00
[52] U.S. Cl. ...................................................... 73/4 R
[58] Field of Search ............................ 73/4 R, 748, 756

[56] References Cited

U.S. PATENT DOCUMENTS

| | | | |
|---|---|---|---|
| 180,625 | 8/1876 | Osborne | 73/4 R |
| 3,164,979 | 1/1965 | Siegel | 73/4 R |
| 3,436,955 | 4/1969 | Wilcher | 73/4 R |

*Primary Examiner*—Donald O. Woodiel

*Attorney, Agent, or Firm*—Hill, Van Santen, Steadman, Chiara & Simpson

[57] ABSTRACT

A method and apparatus for determining the accuracy of a sphygmomanometer whereby the user attaches the sphygmomanometer pressure gauge in an airtight manner onto one end of an air passageway located in a stand, draws a known volume of air through a venting valve attached to the other end of the passageway and into a syringe attached to the venting valve, injects the known volume of air into the sphygmomanometer pressure gauge via the passageway and determines the pressure reading on the face of the pressure gauge. If necessary, the user adjusts the bellows of the pressure gauge to correspond with the reading marked on the syringe and repeats the procedure for different air volumes and pressures.

10 Claims, 4 Drawing Figures

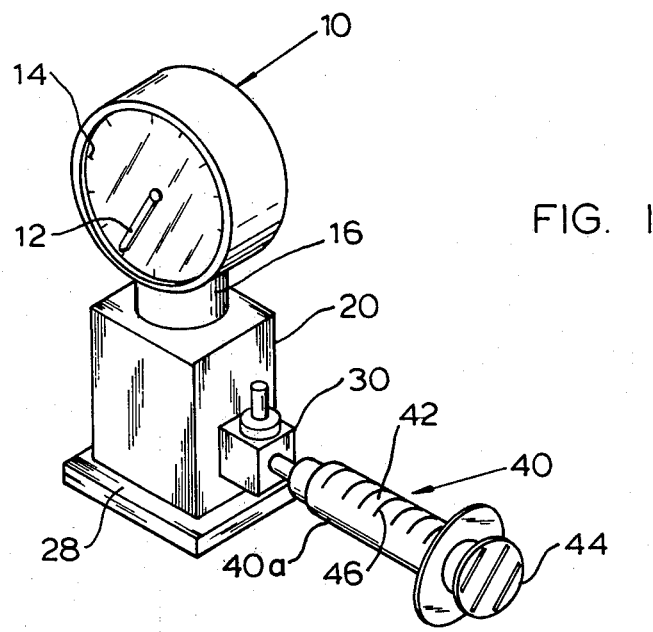
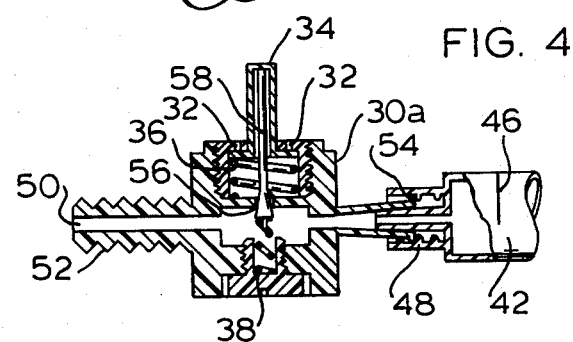
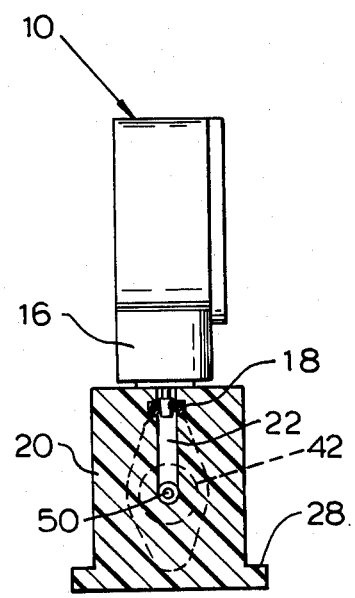
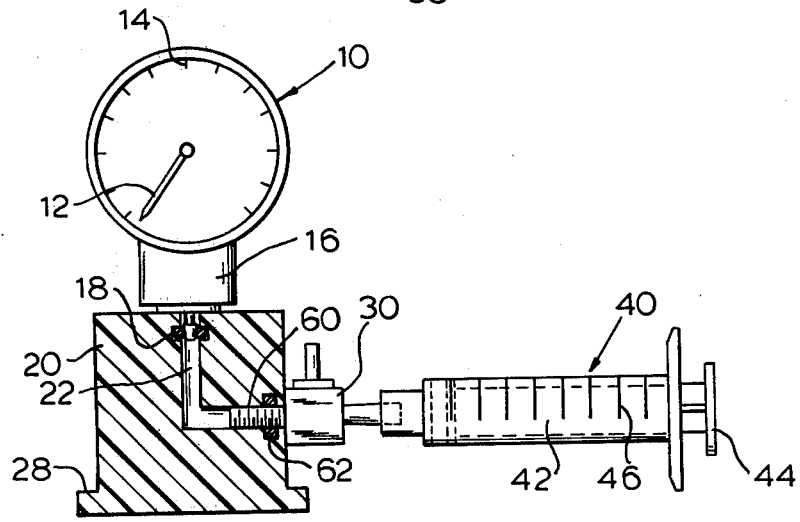

METHOD AND APPARATUS FOR DETERMINING THE ACCURACY OF A SPHYGMOMANOMETER

BACKGROUND OF THE INVENTION

1. Field of the Invention

This invention relates to a method of calibrating or checking the accuracy of a pressure gauge and more specifically to a method and apparatus for calibrating or checking the accuracy of a sphygmomanometer pressure gauge.

2. Description of Prior Art

A sphygmomanometer is a device used by physicians and medical personnel to measure the blood pressure of a patient. Sphygmomanometers were previously constructed so as to have a mercury column which was used to measure the blood pressure. Sphygmomanometers must be accurate since medical personnel prescribe treatments and/or medication on the basis of a patient's blood pressure and even a minor error or inaccuracy in the indicated blood pressure may result in harm to the patient. The mercury column-sphygmomanometer was easily checked for accuracy by adjusting the zero level of the mercury column, as by changing the amount of mercury in the reservoir when no pressure was supplied. With advancements in the art of sphygmomanometers, the mercury column was abandoned in favor of a more compact pressure gauge operated by means of a bellows mechanism to measure blood pressure. However, such pressure gauge-sphygmomanometers are sensitive to mechanical abuse and must be regularly checked for accuracy.

The present method of calibrating or checking the accuracy of a sphygmomanometer pressure gauge consists of removing the pressure gauge from the sphygmomanometer device and securing it to an upper leg of a Y-tube, the other upper leg being connected to a column of mercury and the lower leg of the tube being connected to a source of variable air pressure. A certain known pressure is applied to the lower leg of the tube and transmitted to both the column of mercury and the sphygmomanometer pressure gauge and a comparison is made between the column of mercury and the dial indicia on the face of the pressure gauge to determine the accuracy of the pressure gauge. Various pressures can be applied, allowing for the determination of the accuracy of a pressure gauge throughout a range of pressures. Many sphygmomanometer users or owners do not have such a calibrating or accuracy testing device because of its size and costs. Therefore, these users or owners must return their sphygmomanometers either to the factory or a factory authorized service facility in order to have the accuracy of their sphygmomanometer checked and calibrated.

Because of the widespread use of sphygmomanometers with bellows-operated pressure gauges, the assignee of this patent application alone receives on the order of about 100 of such pressure gauges per day for testing and calibration. Thus, the need for a means by which owners and users of sphygmomanometers can easily and economically check the accuracy and calibrate their own sphygmomanometer pressure gauges is clearly present.

SUMMARY OF THE INVENTION

The present invention provides an improvement over the existing art in that it provides for a handy, low-cost and easy to use method and apparatus for determining the accuracy of a sphygmomanometer.

In accordance with the principles of the invention, one embodiment of the invention comprises a method whereby a bellows-operated pressure gauge is removed from a sphygmomanometer device and attached to one end of a constant volume air passageway contained in a stand, with the other end of the passageway communicating with a calibrated syringe having a barrel with marks thereon corresponding to select pressure values on the sphygmomanometer pressure gauge. The syringe plunger is withdrawn to a select mark and receives a corresponding amount of air therein which is then displaced through the air passage and into the sphygmomanometer pressure gauge by returning the plunger all the way into the syringe barrel. In the event that the sphygmomanometer pressure gauge reading corresponds to that on the syringe, the instrument is deemed accurate. In the event that such readings do not correspond, the sphygmomanometer pressure gauge bellows are adjusted so as to reflect a corrected reading. This method can be repeated for various pressure values to check the accuracy of the sphygmomanometer pressure gauge over a range of pressures.

Another embodiment of the invention comprises an apparatus or device comprised of a stand with a constant volume air passageway contained therein, a sphygmomanometer pressure gauge, a venting valve and a common medical syringe all connectable via the air passageway in an airtight manner in an operable relation. The venting valve may be connected to one end of the air passageway with the syringe being connected to the venting valve. The sphygmomanometer pressure gauge is connected to the opposite end of the air passageway. The syringe barrel contains pressure markings thereon. This device is small, economical and accurate.

BRIEF DESCRIPTION OF THE DRAWINGS

FIG. 1 is a perspective view of a sphygmomanometer pressure gauge attached to a device utilized in the practice of the invention in measuring the accuracy of the gauge.

FIG. 2 is an elevated, partially cross-sectional front view of the assembly shown in FIG. 1.

FIG. 3 is an elevated, partially cross-sectional side view, with some parts shown in phantom, of the assembly shown in FIG. 1.

FIG. 4 is a section view of a venting valve utilized in a preferred embodiment of the invention.

DESCRIPTION OF THE PREFERRED EMBODIMENTS

A setup for checking the accuracy and/or calibrating a sphygmomanometer pressure gauge is shown in FIGS. 1, 2 and 3. A more or less conventional sphygmomanometer pressure gauge is shown generally at 10 which includes on its face an indicator 12 and indicia or pressure markings 14. The sphygmomanometer pressure gauge 10 has a narrow neck 16 which is placed in an air-impermeable manner on an open end of an air passageway 22. The air passageway 22 is of a constant volume and is located within a body member or stand 20. The air passageway 22 has an opening on an outer surface, such as the upper surface of the stand 20 which can be provided with a snap O-ring 18 for an airtight fitting between the sphygmomanometer pressure gauge neck 16 and the air passageway 22. The air passageway 22 communicates at an opposite end with an outer surface of the stand 20 which is spaced apart from the first opening in the surface of the stand. The stand 20 can be supported by a base 28.

The method of calibrating and checking the accuracy of the sphygmomanometer pressure gauge 10 comprises removing the bellows-operated sphygmomanometer pressure gauge 10 having a neck portion 16 and an indicator 12 and pressure indicia 14 on a face therewith from a sphygmomanometer device. The neck portion 16 of the sphygmomanometer pressure gauge 10 is mounted in an airtight manner on one end of the constant volume air passageway 22 located in the stand 20. The air passageway 22 communicates at an opposite end thereof with a source of variable air pressure 40. A known air pressure is introduced from the air pressure source 40 through the air passageway 22 into the sphygmomanometer pressure gauge 10. The pressure reading is monitored from the face of the sphygmomanometer pressure gauge 10 against the known air pressure. If the pressure reading from the face of the sphygmomanometer pressure gauge 10 does not correspond with the known air pressure, the bellows of the sphygmomanometer pressure gauge 10 may be adjusted for example as by means of a mechanical screw contained within the neck portion of the sphygmomanometer pressure gauge. Additional readings may be taken at different known air pressures to test the accuracy of the sphygmomanometer pressure gauge over its operable range of pressure values.

A preferred embodiment of the pressure source can be a conventional syringe 40a comprising a barrel 42 having opposing ends, a mating plunger 44 axially movable within the barrel in an airtight manner so that one end of the plunger extends beyond the barrel, the opposing open end matingly attaching to the air passageway 22 in an airtight manner. The barrel 42 of the syringe 40a contains indicia markings 46 which correspond to pressure readings indicated on the face of the sphygmomanometer pressure gauge 10.

The plunger 44 is operable between a first empty position where the barrel will contain a minimum amount or volume of air and a second full position where the barrel will contain a maximum amount or volume of air. During operation, the end of the plunger which is within the barrel 42 of the syringe 40a will be withdrawn to a select position adjacent to the indicia marking 46 located between the first and second position which corresponds to a given pressure value and a given select volume. The plunger will then be returned to the first position compressing the selected air volume to a second selected air volume and the pressure reading on the face of the sphygmomanometer pressure gauge 10 is compared with the selected syringe pressure value and adjustment can be made, if necessary. In this manner, the syringe contains pressure-related calibrations indicia visible on an outer surface thereof, allowing a user to readily determine the accuracy of a given sphygmomanometer, without the need for pressure gauge readings to determine the air pressure being supplied to the sphygmomanometer.

The use of a syringe as the pressure source requires that air be drawn into the barrel 42 which could create a negative pressure or vacuum within the sphygmomanometer pressure gauge 10. To avoid this problem with this type of a pressure source, a venting means 30 located between the syringe 40a and the sphygmomanometer pressure gauge 10 is provided to prevent formation of a vacuum within the sphygmomanometer pressure gauge while drawing air into the syringe. Various other types of selectively variable pressure sources including constantly positive pressure sources may also be used.

A venting means such as a valve means 30a can be attached to the stand 20 at the opening of the air passageway 22 in a permanent airtight manner. The venting means could also comprise a manually sealable hole or the like positioned along the air passageway or in the syringe barrel or the syringe plunger 44. During operation, such venting means would be opened to outside atmosphere while air is being drawn into the syringe 40a and then closed while the drawn-in volume of air (corresponding to a known pressure) is introduced to the sphygmomanometer pressure gauge.

A preferred embodiment of the venting means 30 may comprise a commercially available venting valve 30a, as shown in FIG. 4. This valve contains an air chamber 50 through which the air can flow from the syringe 40a to the air passageway 24 in the stand 20. In order to draw air into the syringe 40a without causing a vacuum in the sphygmomanometer pressure gauge 10, the venting valve allows for the introduction of air into the air chamber 50 through a pair of air holes 32, which provide select communication between the interior of the chamber 50 and outside atmosphere. Air is drawn through these holes while drawing air into, for example, the syringe 40a by pressing down on an outer stem 34 causing springs 36 and 38 to compress, creating an air permeable opening at 56 between an inner stem 58 and the wall of the air chamber 50. When downward pressure is removed from the outer stem 34, the springs 38 and 36 return the inner stem 58 to its original position and close off the air opening 56 to outside atmosphere. The venting valve 30a can be attached to the stand 20 by means of a threaded end 52 engaging with a female thread 60 or an O-ring 62 in the air passageway 24 of the stand or by a combination of both a thread and an O-ring.

In another embodiment, the syringe 40a can be attached to a venting means 30 via mating luer locks. A female luer lock 48 can be molded as a part of the syringe means, and a mating male luer lock 54 can be molded onto a venting means 30, which may be a more or less conventional air-bleed valve.

As is apparent from the foregoing specifications, the invention is susceptible of being embodied with various alterations and modifications which may differ particularly from those that have been described in the preceeding specification and description. For this reason, it is to be fully understood that all of the foregoing is intended to be merely illustrative and is not to be construed or interpreted as being restrictive or otherwise limited of the present invention, except as it is set forth and defined in the hereto appended claims.

I claim as my invention:

1. A method of calibrating and checking the accuracy of a sphygmomanometer pressure gauge comprising: removing a bellows-operated sphygmomanometer pressure gauge having a neck portion and an indicator and pressure indicia on a face thereof from a sphygmomanometer device; mounting said neck portion of said sphygmomanometer pressure gauge in an air tight manner on one end of a constant air passageway located in a body member, said passageway communicating at an opposite end thereof with a source of variablee air pressure; generating an air pressure in said source of variable air pressure by compressing a selected air volume to a second selected volume within said air pressure source; determining said air pressure by the amount of compression and not by means of a pressure gauge; introducing said known air pressure from said air pressure source through said passageway into said sphygmomanometer pressure gauge; monitoring the pressure reading from said face of said sphygmomanometer pressure gauge against said known air pressure; and adjusting said bellows of the sphygmomanometer pressure gauge to conform with said known air pressure.

2. A method of calibrating and checking the accuracy of a sphygmomanometer pressure gauge comprising: removing a bellows-operated sphygmomanometer pressure gauge having a neck portion and an indicator and pressure indicia on a face thereof from a sphygmomanometer device; mounting said neck portion of said sphygmomanometer pressure gauge in an air tight manner on one end of a constant volume air passageway located in a body member, said passageway communicating at an opposite end thereof with a source of variable air pressure; introducing a known air pressure from said pressure source through said passageway into said sphygmomanometer pressure gauge; whereby said known air pressure is introduced into said air passageway by attaching a syringe means comprising a barrel having opposing open ends, a mating plunger axially moveable within said barrel in an air tight manner so that one end of said plunger extends beyond said barrel, said opposing open end matingly attaching to said air passageway, said plunger operable between a first empty position and a second full position, said barrel having pressure-related calibration indicia visible on an outer surface thereof between said first and second positions; withdrawing said plunger of said syringe means to a selected position so that an end of said plunger within said barrel is adjacent a select calibration indicia on said syringe barrel between said first and second positions; and returning said plunger to said first position; monitoring the pressure reading from said face of said sphygmomanometer pressure gauge against said known air pressure; and adjusting said bellows of the sphygmomanometer pressure gauge to conform with said known air pressure.

3. The method of claim 2 whereby air is introduced into said syringe means by connecting a venting means in operable relation between said syringe means and said sphygmomanometer pressure gauge in an airtight manner; opening said venting means to outside atmosphere while withdrawing said plunger of said syringe means to said select position within said syringe barrel; closing said venting means to outside atmosphere and thereafter returning said plunger to said first position.

4. The method of claim 2 whereby said process is repeated at least once for at least two different known air pressures to test the accuracy over a range defined by said two different pressures.

5. A device for calibrating and testing the accuracy of a sphygmomanometer pressure gauge containing a neck portion therein, comprising a body member having a constant volume air passageway therein, said passageway having opposite ends thereof in communication with atmosphere at two spaced-apart outer surface locations on said body member, said neck portion of said sphygmomanometer pressure gauge being connected in an air tight manner to a first end of said passageway and a source of selectively variable air pressure comprising a means for capturing a select volume of air and compressing it to a second select volume allowing the determination of the air pressure to be made by reference to the amount of compression without referring to a pressure gauge, and being selectively attachable in an air tight manner to said passageway at a second end of said passageway whereby there is fluid communication between said sphygmomonometer pressure gauge and said source of air pressure.

6. A device for calibrating and testing the accuracy of a sphygmomonometer pressure gauge containing a neck portion therein, comprising a body member having a constant volume air passageway therein, said passageway having opposite ends thereof in communication with atmosphere at two spaced-apart outer surface locations on said body member, said neck portion of said sphygmomonometer pressure gauge being connected in an air tight manner to a first end of said passageway, said first end of said air passageway being provided with a snap O-ring to receive said neck of said sphygomonometer pressure gauge in an air tight manner, and a source of selectively variable air pressure selectively attachable in an air tight manner to said passageway at a second end of said passageway whereby there is fluid communication between said sphygmomonometer pressure gauge and said source of air pressure.

7. A device for calibrating and testing the accuracy of a sphygmomonometer pressure gauge containing a neck portion therein, comprising a body member having a constant volume air passageway therein, said passageway having opposite ends thereof in communication with atmosphere at two spaced-apart outer surface locations on said body member, said neck portion of said sphygmomonometer pressure gauge being connected in an air tight manner to a first end of said passageway and a source of selectively variable air pressure selectively attachable in an air tight manner to said passageway at a second end of said passageway wherein the source of variable air pressure is a syringe means comprising a barrel, said barrel having opposing open ends; a mating plunger axially moveable within said barrel in an air tight manner so that one end of said plunger extends beyond said barrel; said opposing open end matingly attaching to said air passageway in an air tight manner, said plunger operable between a first empty position and said second full position and said barrel containing a plurality of pressure-related calibration indicia visible on an outer surface thereof between said first and second positions, selectively attachable in an air tight manner to said passageway at a second end of said passageway at a second end of said passageway whereby there is fluid communication between said sphygmomonometer pressure gauge and said source of air pressure.

8. The device of claim 5 wherein a venting means is provided between said sphygmomanometer pressure gauge and said source of selectively variable air pressure.

9. The device of claim 8 wherein said venting means comprises an airtight air chamber connecting said air passageway of said body member with said source of air pressure in a fluid permeable manner; air holes leading from said chamber to outside atmosphere; axially moveable valve means positioned within said chamber in operative relation with said holes, said valve means being biased in a given direction against a surface of said chamber containing said holes so as to normally seal said holes in an airtight manner, whereby said air holes are selectively opened by axial movement of said valve means in a direction opposite said given direction and provide communication between said chamber and outside atmosphere.

10. A device for calibrating and testing the accuracy of a sphygmomonometer pressure gauge containing a neck portion therein, comprising a body member having a constant volume air passageway therein, said passageway having opposite ends thereof in communication with atmosphere at two spaced-apart outer surface locations on said body member, said neck portion of said sphygmomonometer pressure gauge being connected in an air tight manner to a first end of said passageway and a source of selectively variable air pressure selectively attachable in an air tight manner to said passageway at a second end of said passageway whereby there is fluid communication between said sphygmomonometer pressure gauge and said source of air pressure and a venting means is provided between said sphygmomonometer pressure gauge and said source of selectively variable air pressure, wherein said venting means is attached to said source of air pressure by way of mating male and female luer locks, one of said locks being molded onto said venting means and the other of said locks being molded onto said source of air pressure so that when said luer locks are mated, an air tight seal to outside atmosphere is defined between said source of air pressure and said venting means.

* * * * *